US00PP20902P2

(12) United States Plant Patent
Membrey

(10) Patent No.: US PP20,902 P2
(45) Date of Patent: Mar. 30, 2010

(54) ***DIANELLA* PLANT NAMED 'DINKY DI'**

(50) Latin Name: *Dianella revoluta*
Varietal Denomination: Dinky Di

(75) Inventor: Stephen Membrey, 19 Bangor Drive, Frankston, Victoria (AU) 3199

(73) Assignee: Stephen Membrey, Gayle Membrey Frankston (AU)

( * ) Notice: Subject to any disclaimer, the term of this patent is extended or adjusted under 35 U.S.C. 154(b) by 103 days.

(21) Appl. No.: 11/890,187

(22) Filed: Aug. 4, 2007

(51) Int. Cl.
*A01H 5/00* (2006.01)

(52) U.S. Cl. ..... Plt./424

(58) Field of Classification Search ..... Plt./424
See application file for complete search history.

*Primary Examiner*—Kent L Bell
(74) *Attorney, Agent, or Firm*—Mark P. Bourgeois

(57) ABSTRACT

A new and distinct cultivar of *Dianella* plant named 'Dinky Di' characterized by an upright plant habit, blue-green leaves, dense shoots with short and narrow leaf blades, a short overall height and pale blue flowers.

1 Drawing Sheet

Botanical Classification: *Dianella revoluta*
Variety Denomination: 'Dinky Di'

BACKGROUND OF THE INVENTION

The present Invention relates to a new and distinct cultivar of *Dianella* plant, botanically known as *Dianella revoluta,* and hereinafter referred to by the name 'Dinky Di'. The new cultivar was discovered and selected as a single plant growing within a bed of *Dianella* plants. The exact parents are unknown. The cultivar 'Dinky Di' was discovered in 2003 in Dromana in the state of Victoria, Australia.

The first asexual reproduction of the new *Dianella* was in 2003 by division in Dromana, Victoria, Australia. The unique features of this new *Dianella* are stable and reproduced true to type in successive generations of asexual reproduction.

SUMMARY OF THE INVENTION

The following traits have been repeatedly observed and are determined to be the unique characteristics of 'Dinky Di'. These characteristics in combination distinguish 'Dinky Di' as a new and distinct cultivar:

1. An upright plant habit.
2. Blue-green leaf color.
3. Dense shoots with short and narrow leaf blades.
4. Short overall height.
5. Pale blue flowers on stems up to 17 cm. high.

The closest comparison cultivar is *Dianella* 'DR5000'. *Dianella* 'Dinky Di' is different from 'DR5000' in the following characteristics:

1. 'Dinky Di' has a more compact habit than 'DR5000'.
2. 'Dinky Di' has shorter and narrower leaves than 'DR5000'.
3. 'Dinky Di' has denser shoots than 'DR5000'.

BRIEF DESCRIPTION OF THE PHOTOGRAPH

The accompanying photograph illustrates the distinguishing traits of *Dianella* 'Dinky Di'. The photograph is an overall view of an 8 month old plant. The photograph was taken using conventional techniques and although colors may appear different from actual colors due to light reflectance, it is as accurate as possible by conventional photographic techniques.

DETAILED BOTANICAL DESCRIPTION

The new *Dianella* has not been observed under all possible environmental conditions. The phenotype may vary somewhat with variations in environment such as temperature and light intensity, without, however, any variance in genotype.

The following is a detailed description of the new *Dianella* cultivar named 'Dinky Di'. Data was collected Dromana, Victoria, Australia from plants raised in 150 mm. pots in commercial grade, soil-less potting mix. In the following description, color references are made to The Royal Horticultural Society Colour Chart, 1995 Edition.

Botanical classification: *Dianella revolua* cultivar 'Dinky Di'.

Parentage:
- *Female parent.*—Unknown.
- *Male parent.*—Unknown.

Propagation: Tissue Culture or Division.

Root description: Fine and fibrous.

Plant description.
- *Plant form.*—Upright perennial herb.
- *Plant height.*—11 cm.
- *Plant width.*—About 9 cm.

Growth habit: Erect, very short to approx 11 cm with very dense shoots.

Leaves:
- *Leaf blade.*—Attitude erect, width narrow to maximum 1 cm, length 6 to 8 cm, upper side color yellow-green (141A), lower side color yellow-green (141A to 141B), glaucosity strong, resulting in blue-green overall appearance, shape ligulate, venation parallel, not prominent. apex acute, base rounded, cross section concave, margin flat with small, irregular cilia. Basal sheath: length 1 to 2 cm, width 4 to 6 mm, color: 141A, Anthocyanin coloration absent.

Flowers: Flowers on panicles up to 17 cm. high typically developing in spring through summer and early fall; 10- 16 flowers on each panicle.

*Flower bud.*—shape: ovate, length: 7-10 mm., width: 1-2 mm., color: 77A.

*Flower.*—Diameter: 12-18 mm., height: 8-10 mm., perianth violet (88B); tepals: six in number, shape: ovate, 6-12 mm. in length, 3-4 mm. in width, apex: acute, base: rounded, margin: entire, texture: smooth (both surfaces), color: 88B.

Reproductive organs: stamens, six in number, 5-8 mm. in length, with swollen filaments 2-3 mm. in length, color: 137A, anther color 6A, ovary: position: superior, diameter: 2 mm., color: 137A. Peduncle: length: 17 cm., diameter: 4-8 mm., color: 137A. Pedicel: length: 8-12 mm., diameter: 1-2 mm., color: 137A.

Fruit/Seed: Fruit and/or seed production has not been observed.

Disease/pest resistance: Disease and pest resistance has not been observed.

Temperature tolerance: Plants of the new Dianella have been observed to tolerate temperatures ranging from 0 to 35 degrees. C.

I claim:

1. A new and distinct variety of *Dianella* plant named 'Dinky Di', as described and illustrated.

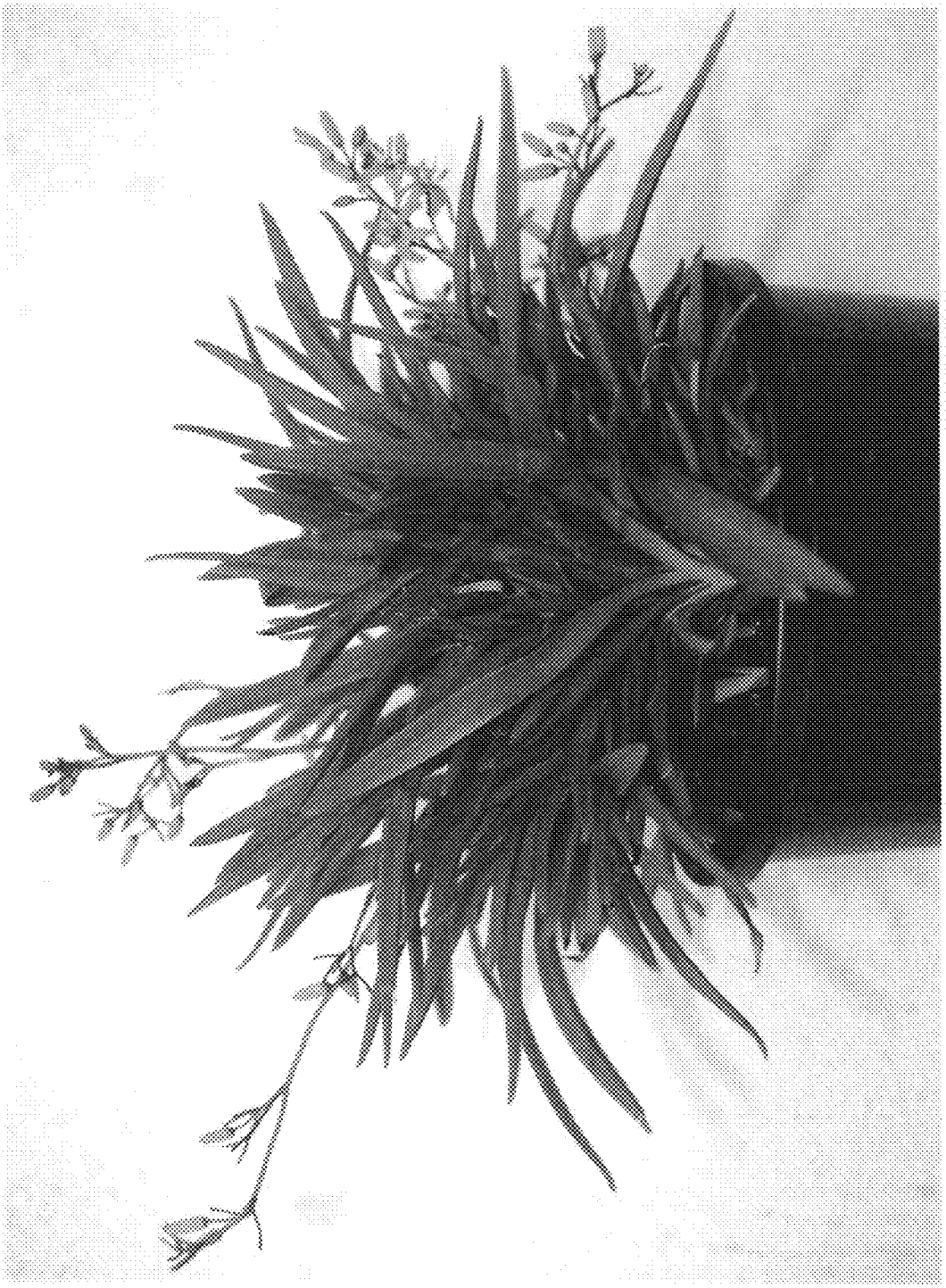

* * * * *